United States Patent
Dorobek et al.

(10) Patent No.: US 7,122,184 B2
(45) Date of Patent: Oct. 17, 2006

(54) SPECIFIC MONOCLONAL ANTIBODY AGAINST TERBINAFINE

(75) Inventors: Birgit Dorobek, Schopfheim (DE); Peter Nussbaumer, Maria Enzersdorf (AT)

(73) Assignee: Novartis AG, Basel (CH)

( * ) Notice: Subject to any disclaimer, the term of this patent is extended or adjusted under 35 U.S.C. 154(b) by 556 days.

(21) Appl. No.: 10/203,076

(22) PCT Filed: Feb. 12, 2001

(86) PCT No.: PCT/EP01/01535

§ 371 (c)(1), (2), (4) Date: Aug. 6, 2002

(87) PCT Pub. No.: WO01/59458

PCT Pub. Date: Aug. 16, 2001

(65) Prior Publication Data

US 2003/0087323 A1    May 8, 2003

(30) Foreign Application Priority Data

Feb. 14, 2000  (GB) .................................. 0003360.5

(51) Int. Cl.
*A61K 39/395*   (2006.01)
(52) U.S. Cl. ............................. 424/141.1; 424/139.1; 435/326; 435/344.1; 530/388.9
(58) Field of Classification Search ............ 424/133.1, 424/139.1; 530/387.3, 388.5; 435/7.1
See application file for complete search history.

(56) References Cited

U.S. PATENT DOCUMENTS 5,169,773 A * 12/1992 Rosenthaler et al. ........ 435/345
5,817,875 A * 10/1998 Karimian et al. ............ 564/387

FOREIGN PATENT DOCUMENTS

| DE | 3316093 | 11/1983 |
|----|---------|---------|
| GB | 2 256 139 A | 12/1992 |
| WO | WO 94/20082 | 9/1994 |
| WO | WO 94/23018 | 10/1994 |
| WO | WO 97/49732 | 12/1997 |

OTHER PUBLICATIONS

Campbell, A. "Monoclonal Antibody Technology" (1984) Elsevier Science Publishing Company, Inc., pp. 1-32.*
Stewart et al., "Titering antibodies" in Current Protocols in Cytometry, (1997) John Wiley and Sons, 4.1.1-4.1.13.*
The Immunoassay Handbook, second edition, edited by David Wild (2001) Nature Publishing Group, pp. 83-89.*
Janeway et al., Immunobiology,3rd edition 1997, Garland Publishing Inc., pp. 2:2-2:4, 2:17, and 2:18.*
Kuby et al., "Immunology", 1992, W. H. Freeman and Company, p. 125.*
Köhler et al., "Continuous Cultures of Fused Cells secreting Antibody of Predefined Specificity", *Nature*, vol. 256, pp. 495-497 (1975).
Battig et al., "Pharmacokinetics and Biotransformation of the $^{14}$C-Labeled Drug in Laboratory Animals and Man", *Proc. Int. Congr. Chemother.*, 13th, Part 116, pp. 37-40 (1983).
Stütz et al., "Synthesis and Antifungal Activity of (E)-N-(6,6-Dimethyl-2-hepten-4-ynyl)-N-methyl-1-napththalenemethanamine (SF-86-327) and Related Allylamine Derivatives with Enhanced Oral Activity", *J. Med. Chem.*, vol. 27, pp. 1539-1543 (1984).
Schuster, "Metabolic Degradation of Terbinafine in Liver Microsomes from Man, Guinea Pig and Rat", In: Recent Trends in the Discovery, Development and Evaluation of Antifungal Agents, Fromtling, Editor, J.R. Prous Science Publishers S.A., Barcelona, pp. 461-470 (1987).
Battig et al., "Major Biotransformation Routes of Some Allylamine Antimycotics", In: Recent Trends in the Discovery, Development and Evaluation of Antifungal Agents, Fromtling, Ed., J.R. Prous Science Publishers S.A., Barcelona, pp. 479-495 (1987).
Schatz et al., "Analytical Methods for the Determination of Terbinafine and Its Metabolites in Human Plasma, Milk and Urine", *Drug Res.*, vol. 39, Suppl. I, No. 4, pp. 527-532 (1989).
Nussbaumer et al., "Allylamine Antimycotics: Recent Trends in Structure-Activity Relationships and Syntheses", *Pestic. Sci.*, vol. 31, pp. 437-455 (1991).
The Immunoassay Handbook, Concepts 89, "Cross-Reactivity".
Denouël et al., "Determination of Terbinafine and Its Desmethyl Metabolite in Human Plasma by High-Performance Liquid Chromatography", *J. Chromatogr. B.*, vol. 663, pp. 353-359 (1995). (XP-002168314).
Watanabe et al., "Development of a Competitive Enzyme-Linked Immunosorbent Assay Based on a Monoclonal Antibody for a Fungicide Flutolanil", *Analytica. Chimica. Acta.*, vol. 376, pp. 93-96 (1998).

(Continued)

*Primary Examiner*—G. R. Ewoldt
*Assistant Examiner*—Michael Szperka
(74) *Attorney, Agent, or Firm*—Gregory C. Houghton

(57) ABSTRACT

The invention concerns momoclonal antibodies to terbinafine in free base or salt form, immunogenic conjugates suitable for preparing them, hybridoma capable of producing them, and corresponding assay kits. The antibodies can be prepared by administering to an appropriate animal an immunogenic conjugate of a suitable derivative of terbinafine covalently linked to an immonogen, recovering antibody-producing cells sensitized to the conjugate, immortalizing the antibody-producing cells, selecting a resultant immortalized cell line, and recovering the resultant antibodies therefrom. They are indicated for use in particular in the measurement of terbinafine tissue concentration and distribution in bodily fluids or compartments, especially nails.

4 Claims, 1 Drawing Sheet

OTHER PUBLICATIONS

Instructions, "Imject® Carboxyl Reactive Antibody Production & Purification Kits with KLH, BSA or OVA", Pierce, Rockford, IL, pp. 1-7 (1999). (XP-002168315).

Machard et al., "A Sensitive Amphotericin B Immunoassay for Pharmacokinetic and Distribution Studies", Antimirobial Agents and Chemotherapy, vol. 44, pp. 546-550 (2000). (XP-000999851).

Watanabe et al., "Development of an Enzyme-Linked Immunosorbent Assay for the Fungicide Imazalil in Citrus Fruits", *J. Agric. Food Chem.*, vol. 48, pp. 5124-5130 (2000).

Watanabe et al., "Immunoaffinity Column Clean-Up for the Determination of Imazalil in Citrus Fruits", *Analytica. Chimica. Acta.*, No. 433, pp. 199-206 (2001).

Derwent Abstract AN 1998-077113, Bizzini et al., WO 9749732, Jun. 26, 1997.

Derwent Abstract AN 1998-560719, Kenkyusho, JP 10248565A, Mar. 18, 1997.

Derwent Abstract AN 1993-284687, JP 05199894 A, Aug. 20, 1990.

Chemical Abstracts, vol. 104, pp. 11434-11435 (1986).

\* cited by examiner

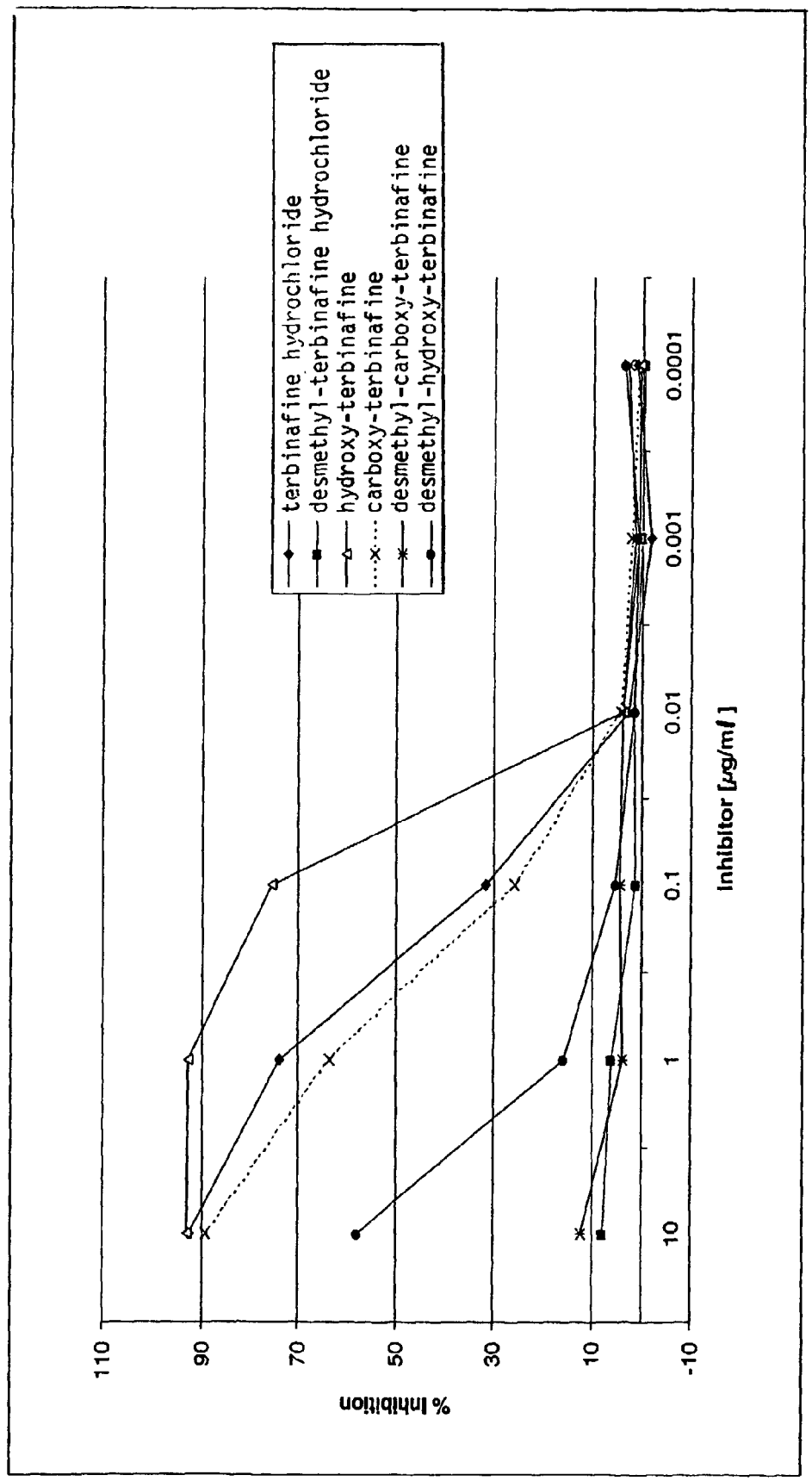
Figure 1: Crossreactivity (LAM-IA)

SPECIFIC MONOCLONAL ANTIBODY AGAINST TERBINAFINE

CROSS-REFERENCE TO RELATED APPLICATIONS

This application is the national stage entry of PCT/EP01/01535, filed Feb. 12, 2001, undr 35 U.S.C. 371, which claims priority from the foreign application filed in Great Britain on Feb. 14, 2000.

BACKGROUND OF THE INVENTION

The invention relates to monoclonal antibodies.

It concerns monoclonal antibodies to terbinafine (Lamisil®), i.e. to (E)-N-(6,6-dimethylhept-2-en-4-ynyl)-N-methyl-1-naphthalene methanamine of formula I

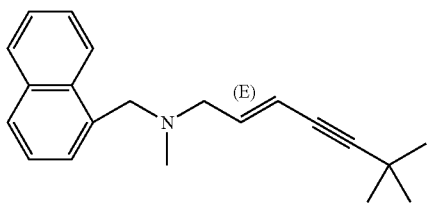

in free form or salt form, particularly hydrochloride salt form, hereinafter briefly named "the antibodies of the invention".

Terbinafine is an antimycotic agent marketed worldwide in both oral and topical formulations, particularly for the treatment of fungal infections of the skin, nail and hair. It is a representative of the allylamine class of synthetic antifungal agents, which is chemically and mechanistically distinct from the other antimycotic drugs used clinically.

One of the advantages of terbinafine resides in its very low immunogenicity. Thus, although it has been on the market for several years, so far no reports have appeared in the literature describing strong immune responses thereto. While this is of clinical benefit, it renders detection of the drug by immunological methods problematic, even when it is coupled to immunogenic protein to enhance immune response.

Further, in view of its widespread use, development of a simple immunoassay procedure allowing easy and speedy detection of terbinafine in body fluids, tissues or compartments of a patient, e.g. serum or nails, would be very desirable. Monitoring e.g. blood or nail levels of terbinafine in patients with particular reference to treatment failure (dermatophytoma) is very desirable for fine tuning of the dosage administered and better understanding of the mode of action so as to maintain the minimum level sufficient for beneficial pharmacological activity in, e.g., onychomycosis. However, there have been no previous reports of monoclonal antibodies which recognize terbinafine, possibly due to inherent difficulties in making such antibodies in view of the low immunogenicity of the drug mentioned above.

BRIEF DESCRIPTION OF THE INVENTION

It has now been found that monoclonal antibodies to terbinafine can be prepared which are surprisingly sensitive to terbinafine, using derivatives of terbinafine covalently linked to an immunogenic protein.

Such derivatives may e.g. be metabolites of terbinafine or further structurally closely related derivatives.

It has also been found that monoclonal antibodies to terbinafine recognizing an epitope on the effector portion of terbinafine can be obtained, using metabolite derivatives of terbinafine which are themselves pharmacologically inactive.

Therefore, the present invention allows development of inmmunologically-based methods for terbinafine detection and dosage, e.g. an assay for terbinafine which is both highly sensitive and specific (see Examples hereunder) as regards the degree of discrimination of the assay between negative and positive samples, i.e., relative affinities of two systems.

BRIEF DESCRIPTION OF THE DRAWINGS

FIG. 1 depicts a Crossreacstivity graph of compounds, terbinafine hydrochloride, desmethyl-terbinafine hydrochloride, hydroxyl-terbinafine, carboxy-terbinafine, desmethyl-carboxy-terbinafine, and desmethyl-hydroxy-terbinafine plotted against inhibitors (%) at terbinafine concentration (mg/ml) as described in the Table labeled Crossreactivity (LAM-JA) in Example 4.

DETAILED DESCRIPTION OF THE INVENTION

The antibodies of the invention are prepared by inoculation of an appropriate animal, e.g. a mouse, with an immunogenic conjugate of a suitable derivative of terbinafine covalently linked to an immunogen, e.g. an immunogenic protein. This may be effected in conventional manner, e.g. along the lines as described by Köler and Milstein (Nature 256 [1975] 495–497). The process conveniently comprises administering the immunogenic conjugate, recovering antibody-producing cells sensitized to the conjugate, immortalizing the antibody-producing cells, e.g. by fusion with a suitable myeloma, selecting a resultant immortalized cell line, and recovering the resultant antibodies of the invention therefrom.

The immunogenic protein is e.g. bovine serum albumin (BSA), ovalbumin (OVA) or keyhole limpet hemocyanin (KLH).

The antibodies of the invention are screened and characterized in conventional manner, e.g. according to their ability to distinguish between terbinafine and its metabolites and derivatives, e.g. by determination of relative cross-reactivity. They may be further characterized by their relative binding affinity to other known antimycotics, e.g. azoles, or amphotericin B. Crossreactivity is herein determined by measurement of antibody response to terbinafine and its metabolite derivatives 1) to 5) listed below and their ability to distinguish between terbinafine and appropriate metabolites [The Immunoassay Handbook, D. Wild, Ed. (1994), Stockton Press, p. 89). Relative crossreactivity is the concentration of analyte giving 50% at the point where the reduction in signal corresponds to 50% of the signal achieved in the absence of analyte (ratio $B/B_0$ of 50%), as a percentage of the analyte concentration giving the same fall in signal.

The following derivatives of terbinafine are prepared:
1) (E)-2,2-dimethyl-7-[methyl(naphthalen-1-ylmethyl)amino]hept-5-en-3-ynoic acid, i.e. compound XXIX on page 443 in Pestic. Sci. 31 (1991) 437–455, hereinafter briefly named "carboxy-terbinafine";

2) (E)-N-(6,6-dimethylhept-2-en-4-ynyl)-1-naphthalenemethanamine, i.e. compound (2) on page 528 in *Arzneim. F./Drug Res.* 39 (1989) 527–532, hereinafter briefly named "desmethyl-terbinafine";
3) (E)-2,2-dimethyl-7-[methyl(naphthalen-1-ylmethyl)amino]hept-5-en-3-yn-1-ol, i.e. compound XXX on page 443 in above *Pestic. Sci.* (op. cit.), hereinafter briefly named "hydroxy-terbinafine";
4) (E)-2,2-dimethyl-7-[(naphthalen-1-ylmethyl)amino]hept-5-en-3-ynoic acid, i.e. compound (4) on page 528 in above *Arznein. F./Drug Res.* (op. cit.), hereinafter briefly named "desmethyl-carboxy-terbinafine"; and
5) (E)-2,2-dimethyl-7-[(naphthalen-1-ylmethyl)amino]hept-5-en-3-yn-1-ol, i.e. compound XXXII on page 443 in above *Pestic. Sci.* (op. cit.), hereinafter briefly named "desmethyl-hydroxy-terbinafine".

A derivative may be in free form or salt form, e.g. hydrochloride acid addition salt form. A particularly suitable derivative of terbinafine is carboxy-terbinafine as defined above.

The starting materials and intermediate compounds are either known or can be prepared according to known methods or analogously as described in the Examples.

A hybridoma cell line designated LAM-JA (11H2.F9.C4) produced from PAI-0 myeloma in mice immunized with BSA protein conjugate of carboxy-terbinafine (see Example 1 hereafter) has been deposited with the Deutsche Sammlung von Mikroorganismen und Zelikulturen GmbH (DSMZ), D-38124 Braunschweig, Germany under the provisions of the Budapest Treaty on Nov. 25, 1999 and has received Accession Number DSM ACC2422.

The invention therefore also concerns:
Antibodies of the invention recognizing an epitope on the effector portion of terbinafine, especially, specifically recognizing terbinafine;
antibodies of the invention whenever prepared from carboxy-terbinafine;
antibodies of the invention whenever prepared from hybridoma LAM-JA (DSM ACC2422);
hybridomas capable of producing antibody of the invention; the hybridoma LAM-JA (DSM ACC2422);
immunogenic conjugates suitable for preparing antibodies of the invention which comprise a derivative of terbinafine covalently linked to an immunogen;
a process for preparing antibodies of the invention which comprises administering to an appropriate animal an immunogenic conjugate of a suitable derivative of terbinafine covalently linked to an immunogen, recovering antibody-producing cells sensitized to the conjugate, immortalizing the antibody-producing cells, selecting a resultant immortalized cell line, and recovering the resultant antibodies therefrom;
Immunoassay kits for the measurement of terbinafine tissue concentration and distribution in bodily fluids or compartments, particularly nails, comprising antibody of the invention.

The following Examples illustrate the invention. All temperatures are in degrees Celsius. The compounds are in free base form unless specified otherwise. The following abbreviations are used:

| BSA | bovine serum albumin |
| ch | hydrochloride acid addition salt form |
| DMSO | dimethylsulfoxide |
| EDC | 1-ethyl-3-(3-dimethylaminopropyl)carbodiimide |
| ELISA | enzyme-linked immunosorbent assay |
| i.p. | intraperitoneally |
| mAb | monoclonal antibody |
| m.p. | melting point |
| OPD | o-phenylenediamine |
| OVA | ovalbumin |
| PBS | phosphate-buffered saline |
| s.c. | subcutaneously |

EXAMPLE 1

Protein Conjugates of Carboxy-terbinafine 4.02 mg carboxy-terbinafine (m.p. 118–120°) is dissolved in 200 µl of DMSO and 800 µl of conjugation buffer (Imject®EDC Conjugation Kit, Pierce) is added carefully to the hapten solution. 500 µl of this mixture is added dropwise with vigorous stirring to the appropriate protein solution (protein concentration 2 mg/ml) of BSA or OVA. Each of the resultant protein-hapten solution (500 µl) is added to 10 mg EDC. The reaction mixture is stirred for 3 hours at room temperature and the resultant conjugates are purified by dialysis at 4° against 4l of PBS, twice over 24 hours. The resultant conjugates (terbinafine-OVA; terbinafine-BSA) are aliquoted and stored at –18°.

EXAMPLE 2

Production of Monoclonal Antibody

Female Balb/C mice (20–25 g) each receive 100 µg carboxy-terbinafine conjugate covalently linked to OVA according to Example 1, in complete Freund adjuvant, administered by i.p. injection. After 5 and 10 weeks a first and second boost comprising one half of the initial amount of the immunogenic conjugate emulsified in incomplete Freund adjuvant is administered by i.p. injection. Direct ELISA (see below) is used to confirm the presence of antibodies reactive to the antigen in the animals' blood serum. After 13 weeks mice receive the third boost by i.p. injection, and ten days later mice receive booster injections comprising 50 µg of the antigen i.v. on days –3, –2 and –1. On day +1 mice are sacrificed and their spleen cells are isolated and fused with e.g. PAI-0 cells or other suitable myeloma line. The resulting hybridoma are cultured and selected using ELISA for expression of antibody having a high affinity to terbinafine. After selection of the cell line with the highest production rate, secreted antibodies are purified with Streamline 25 column system loaded with 75 ml of Streamline-Protein A by expanded bed adsorption chromatography.

EXAMPLE 3

Selection of Antibodies by Direct ELISA for Terbinafine

Microtiter plates are coated with 5 µg/ml terbinafine hydrochloride—protein (BSA) conjugate in carbonate buffer overnight at 4°, then saturated with blocking reagent [SuperBloc® buffer (Pierce)] and washed 3× with 0.05% (v/v) PBS-TWEEN® (polyoxyethylene 20 sorbitan monoleate). The hybridoma supernatants to be screened are diluted in a 1% (w/v) solution of BSA in PBS-TWEEN® (polyoxyethylene 20 sorbitan monoleate), and incubated for 2 hours at 37°. Level of bound antibody is measured by anti-mouse IgG rabbit immunoglobulin coupled to horseradish peroxidase with OPD as the substrate. After incubation for one hour at room temperature the enzymatic substrate is hydrolyzed and absorbance at 490/650 nm is measured after 15 minutes incubation in the dark.

Based on this test the hybridoma cell line designated LAM-JA (11H2.F9.C4) (producing antibody of sublclass IgG2a λ) obtained from Example 2 was selected for antibody production.

EXAMPLE 4

Competitive ELISA for Terbinafine Derivatives

The direct ELISA according to Example 3 above is converted to a competitive ELISA wherein a competitor is added to the monoclonal antibody solution, and binding of the mAB to the conjugate in the presence and absence of the competitor is measured. Standard curves to determine crossreactivity of a selected antibody to terbinafine and its derivatives are prepared using solutions containing known concentrations of terbinafine and appropriate derivatives (e.g. 10 µ/ml to 0.0001 µg/ml in buffer).

The result of such competitive assay for the purified antibodies from hybridoma cell line LAM-JA (where the immunogen used was carboxy-terbinafine coupled to OVA), is as follows:

TABLE

Crossreactivity (LAM-JA)

| Compound | Inhibition (%) at terbinafine concentration (µg/ml) | | | | | |
| --- | --- | --- | --- | --- | --- | --- |
| | 10 | 1 | 0.1 | 0.01 | 0.001 | 0.0001 |
| Terbinafine ch | 92.6 | 73.8 | 31.5 | 2.70 | −1.92 | 0.99 |
| Carboxy-terbinafine | 89.2 | 63.8 | 25.8 | 4.30 | 2.11 | 0.85 |
| Desmethyl-terbinafine ch | 7.87 | 5.96 | 1.22 | 1.55 | −0.14 | −0.45 |
| Hydroxy-terbinafine | 93.0 | 92.9 | 72.5 | 3.74 | 0.56 | 0.40 |
| Desmethyl-carboxy-terbinafine | 12.1 | 3.85 | 4.40 | 3.74 | 1.38 | 2.81 |
| Desmethyl-hydroxy-terbinafine | 58.0 | 15.7 | 5.30 | 1.60 | 0.79 | 3.60 | and is also set out in graphic form in FIG. 1.

The measurement of antibody response to substances other than the analyte is the crossreactivity. It may be "expressed as the point where the reduction in signal corresponds to 50% of the signal achieved in the absence of analyte ($B/B_0$=50%), as a percentage of the analyte concentration giving the same fall in signal" [*The Immunoassay Handbook*, David Wild, Stockton Press, USA, 1994].

% crossreactivity is calculated as follows from FIG. 1:

$$\frac{\text{Concentration of analyte giving 50\% } B/B_0}{\text{Concentration of cross} - \text{reactant giving 50\% } B/B_0}$$

It is apparent from the above results that there is strong crossreactivity against carboxy-terbinafine, the original immunogen, and against hydroxy-terbinafine (≧67%); low crossreactivity against desmethyl-hydroxy-terbinafine (4.5%) and negligible crossreactivity against desmethyl-carboxy-terbinafine and desmethyl-terbinafine (not detectable).

Antibody specificity describes the ability of an antibody to produce measurable response only for the analyte of interest: the above results describe a highly specific antibody.

The antibodies of the invention are indicated for use in a medical setting, e.g. in a suitable assay, particularly in assay kits comprising an antibody of the invention for the measurement of terbinafine tissue concentration and distribution in mycotic infection, expecially in onychomycosis for accurate determination of terbinafine in body fluids or compartments, e.g. nails. Such determination is particularly indicated in onychomycosis, with particular reference to treatment failure (dermatophytoma).

One approach is an ex vivo competitive assay using antibody of the invention and terbinafine tracer. For example, microtiter plates are coated with antibody and exposed to the competitor which is a labeled terbinafine, e.g. fluoro-labeled, radio-labeled, e.g. europium-labeled, or enzyme-labeled, especially biotinylated terbinafine, in the presence and absence of test material believed to contain terbinafine, e.g. plasma, blood, tissue or nails from a patient. The plates are rinsed and the amount of labeled competitor which bound to the antibody is measured. This amount varies inversely with the amount of terbinafine in the test fluid.

Another approach is an ELISA using antibody, a terbinafine conjugate, and a labeled, e.g. enzyme-labeled tracer antibody recognizing murine IgG. For example, microtiter plates are coated with a terbinafine-protein conjugate, e.g. the immunogenic BSA-carboxy-terbinafine conjugate (Example 1), then exposed to antibody in the presence and absence of test material, rinsed, and antibody binding to the terbinafine conjugate is detected by binding of the tracer antibody to the antibody bound to the terbinafine conjugate. Again, the amount of bound antibody will be varying inversely with the amount of terbinafine in the test sample.

In either case, the assay is standardized with test solution containing known concentration of terbinafine.

The invention therefore also comprises an assay kit comprising an antibody of the invention, preferably in lyophilized form or coated onto a microtiter plate. The kit optionally further comprises either a terbinafine protein conjugate, optionally coated onto a plate, and/or a labeled terbinafine derivative. It also optionally comprises a terbinafine solution for standardization and instructions for use. Alternatively, the monoclonal antibodies of the invention may be used in a customized ELISA or other assay system.

As regards the applicability of the above assay in nails, analysis with high performance liquid chromatography (HPLC) and UV detection gave no hint for the presence of the polar metabolites of terbinafine in the nail matrix, i.e. neither hydroxy-terbinafine, nor desmethyl-hydroxy-terbinafine, nor carboxy-terbinafine were found, while desmethyl-terbinafine was measurable. Thus, in relation to the crossreactivities of the antibodies of the invention with the above metabolites (see Example 4), no detection interferences are likely to be encountered with terbinafine in nails.

In another approach enzyme-labeled terbinafine antibody is used in order to localize constituents present in tissues or cells or, alternatively, to demonstrate in the sera or other compartments of patients the presence of antibodies directed against cell constituents, based on the same basic principles as for immunofluorescence methods except that detection of a cytochemical stain specific for the enzyme is used as a marker and replaces fluorescence detection.

The invention claimed is:

1. A monoclonal antibody that binds terbinafine and is prepared from hybridoma LAM-JA, deposited as accession number DSM ACC2422.

2. The hybridoma according to claim 1 which is LAM-JA, deposited as accession number DSM ACC2422.

3. An immunoassay kit for the measurement of terbafine tissue concentration and distribution in bodily fluids or compartments, comprising said antibody according to claim 1.

4. An immunoassay kit according to claim 3 where said compartments are nails.

* * * * *